US011013713B2

(12) United States Patent
Dressman et al.

(10) Patent No.: US 11,013,713 B2
(45) Date of Patent: May 25, 2021

(54) METHOD OF TREATMENT

(71) Applicant: Vanda Pharmaceuticals, Inc., Washington, DC (US)

(72) Inventors: Marlene Michelle Dressman, Gernmantown, MD (US); Louis William Licamele, Potomac, MD (US); Mihael H. Polymeropoulos, Potomac, MD (US)

(73) Assignee: VANDA PHARMACEUTICALS INC., Washington, DC (US)

( * ) Notice: Subject to any disclaimer, the term of this patent is extended or adjusted under 35 U.S.C. 154(b) by 0 days.

(21) Appl. No.: 15/381,025

(22) Filed: Dec. 15, 2016

(65) Prior Publication Data
US 2017/0165222 A1    Jun. 15, 2017

Related U.S. Application Data

(60) Provisional application No. 62/267,860, filed on Dec. 15, 2015.

(51) Int. Cl.
*A61K 31/343*      (2006.01)

(52) U.S. Cl.
CPC .................................. *A61K 31/343* (2013.01)

(58) Field of Classification Search
CPC ................................................... A61K 31/343
See application file for complete search history.

(56) References Cited

U.S. PATENT DOCUMENTS

| 8,785,492 B2 | 7/2014 | Dressman et al. |
| 9,549,913 B2 * | 1/2017 | Dressman ............ A61K 31/343 |
| 2006/0246129 A1 * | 11/2006 | Linardakis ........... A61K 31/198 |
| | | 424/451 |

OTHER PUBLICATIONS

Hardeland, Tasimelteon, a melatonin agonist for the treatment of insomnia and circadian rhythm sleep disorders, 2009, Current Opinion on Investigational Drugs, 10(7), 691-701.*
Finkelstein, Effect of Growth Hormone Therapy on Height in Children with Idiopathic Short Stature, 2002, Arch Pediatr Adolesc Med, vol. 156, pp. 230-240.*
Finkelstein et al. "Age Related Change in the twenty-four hour spontaneous secretion of growth hormone", 1972, Journal of Clinical Endocrinolgy and Metabolism, vol. 35, No. 5, pp. 665-670, Abstract Only Provided. (Year: 1972).*
NCT01430754 (Year: 2011).*
NCT01429116 (Year: 2011).*

* cited by examiner

*Primary Examiner* — Jeffrey S Lundgren
*Assistant Examiner* — Ibrahim D Bori
(74) *Attorney, Agent, or Firm* — Hoffman Warnick LLC

(57) ABSTRACT

Embodiments of the invention relate generally to increasing adult height in individuals with no light perception (NLP).

3 Claims, 2 Drawing Sheets

METHOD OF TREATMENT

CROSS-REFERENCE TO RELATED APPLICATIONS

This application claims the benefit of U.S. Provisional Patent Application Ser. No. 62/267,860, filed 15 Dec. 2015, which is hereby incorporated herein as though fully set forth.

BACKGROUND

The incidence of abnormal circadian rhythms is greater in blind individuals with no light perception (NLP) compared with those with some light perception (LP). Non-24-Hour Sleep-Wake Rhythm Disorder (Non-24) is a chronic circadian rhythm disorder, common in the blind, in which the sleep-wake cycle of affected individuals is in cyclic misalignment (i.e., not synchronized or entrained).

Previous studies have reported that blind people have a reduced height and that those with NPL are shorter than those with some LP. These studies have not, however, examined whether height is related to non-24-hour rhythms or Non-24. Applicant conducted a study to investigate this issue.

BRIEF DESCRIPTION OF THE DRAWINGS

These and other features of this invention will be more readily understood from the following detailed description of the various aspects of the invention taken in conjunction with the accompanying drawings that depict various embodiments of the invention, in which.

It is noted that the drawings of the invention are not to scale. The drawings are intended to depict only typical aspects of the invention, and therefore should not be considered as limiting the scope of the invention.

DETAILED DESCRIPTION

In a study by Applicant to investigate the effect of non-24-hour circadian periods on adult height, a total of 164 patients with NLP were segregated as either having Non-24 (i.e., those having a circadian period >24.1 hours [95% confidence interval, >24.0 h] assessed from urinary 6-sulfatoxymelatonin) or entrained to a 24-hour day. A random sample of 324 individuals were matched for age, sex, and race from the National Health and Nutritional Examination Survey (2013-2014) and used as controls. The age of peak growth rate (PGR) was defined as 12 and 14 years for females and males, respectively. The demographic characteristics of the study participants are shown in Table 1.

TABLE 1

| Characteristic | NLP Patients With Non-24 (n = 110) | NLP Patients, Entrained (n = 54) | Controls (n = 324) |
|---|---|---|---|
| Age, mean (SD), y | 51.1 (13.1) | 46.5 (13.7) | 49.8 (13.3) |
| Sex, n (%) | | | |
| Male | 64 (58.2) | 18 (33.3) | 162 (50.0) |
| Female | 46 (41.8) | 36 (66.7) | 162 (50.0) |

TABLE 1-continued

| Characteristic | NLP Patients With Non-24 (n = 110) | NLP Patients, Entrained (n = 54) | Controls (n = 324) |
|---|---|---|---|
| Race, n (%) | | | |
| White | 87 (79.1) | 41 (75.9) | 246 (75.9) |
| Black | 18 (16.4) | 9 (16.6) | 52 (16.1) |
| Other | 5 (4.5) | 4 (7.4) | 26 (8.0) |
| BMI, mean (SD) | 28.4 (3.8) | 27.8 (3.8) | 26.6 (3.6) |

BMI = body mass index: Non-24 = non-24-hour sleep-wake rhythm disorder: NLP = no light perception; SD = standard deviation.

Figure 1:
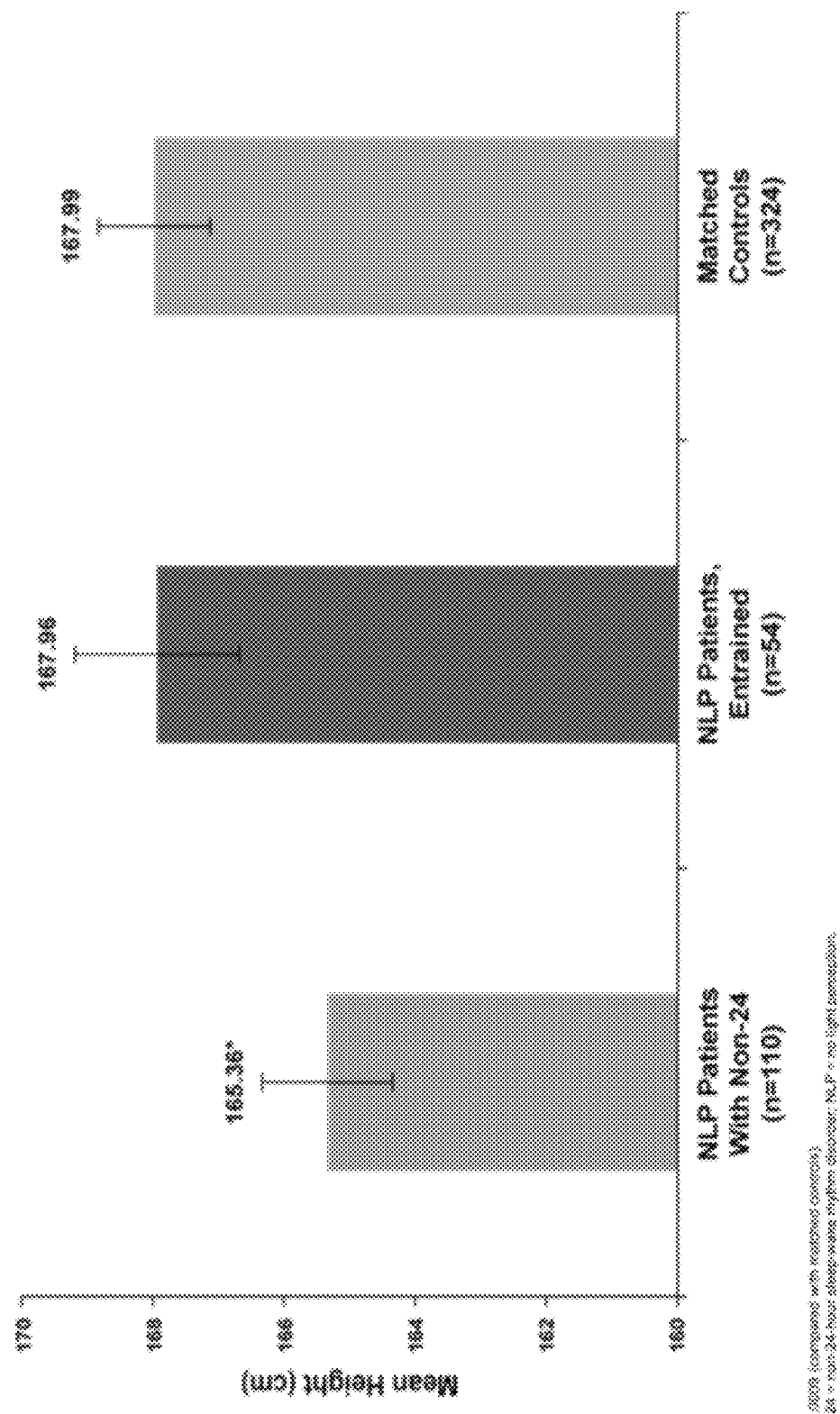
FIG. 1 shows the mean height of NLP individuals and matched controls.

The mean height (in cm) of NLP individuals with Non-24, entrained NLP individuals, and matched controls are shown in FIG. 1. These results showed that NLP individuals with Non-24 were significantly shorter than matched controls (P=0.0009), while there was no significant difference in height between entrained NLP individuals and matched controls (P=0.98). Overall, NLP individuals were significantly shorter than matched controls (P=0.012), although this is likely attributable to the NLP individuals with Non-24.

Among NLP individuals with Non-24, those who lost light perception prior to the age of PGR were shorter than those who lost light perception after the age of PGR (P=0.032). There was no significant difference in height among entrained NLP patients irrespective of the age of light perception loss (P=0.46).

Among individuals who lost light perception prior to the age of PGN, NLP individuals with Non-24 were significantly shorter than entrained NLP patients (P=0.042). There was no significant difference in height among patients with NLP who lost light perception after the age of PGR irrespective of whether they were entrained (P=0.25).

Figure 2:
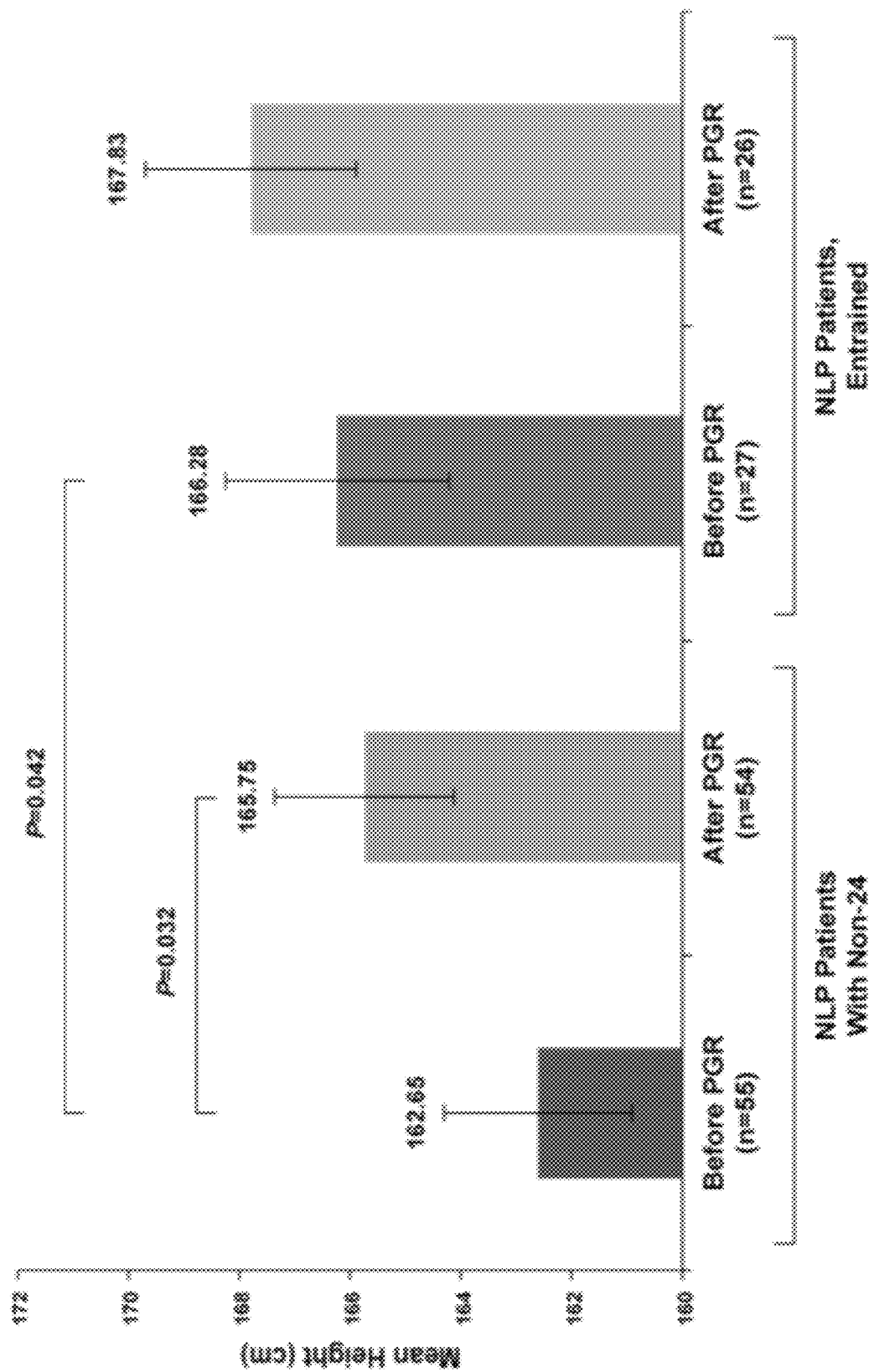
FIG. 2 shows the mean height of NLP individuals, entrained and suffering from Non-24, based on whether light perception was lost prior to or after PGR.

These results are shown in FIG. 2.

The results of Study 2 suggest that non-entrained circadian rhythms may affect growth potential during adolescence.

The treatment of NLP individuals with Non-24 to entrain them to a 24-hour circadian period may therefore have the effect of increasing adult height in such individuals. The entrainment of patients with Non-24 to a 24-hour sleep-wake cycle using tasimelteon is described in U.S. patent application Ser. No. 13/751,011, filed 25 Jan. 2013, which is hereby incorporated herein as though fully set forth.

Tasimelteon is a circadian regulator which binds specifically to two high affinity melatonin receptors, Mel1a (MT1R) and Mel1b (MT2R). These receptors are found in high density in the suprachiasmatic nucleus of the brain (SCN), which is responsible for synchronizing our sleep/wake cycle. Tasimelteon has been shown to improve sleep parameters in prior clinical studies, which simulated a desynchronization of the circadian clock. Tasimelteon has so far been studied in hundreds of individuals and has shown a good tolerability profile.

Treatment of an individual to entrain that individual to a 24-hour sleep-wake cycle and thereby increase adult height may include, for example, administering to an individual who has not yet reached PGR an effective dose of tasimelteon or a pharmaceutically-acceptable salt thereof. According to some embodiments of the invention, such administration may include oral administration. According to some embodiments of the invention, such administration may include administering between 10 mg and 100 mg (e.g., between 20 mg and 50 mg, or 20 mg) of tasimelteon or a pharmaceutically-acceptable salt thereof once daily before (e.g., 0.5 hour to 1.5 hours before) a target sleep time.

As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

This written description uses examples to disclose the invention, including the best mode, and also to enable any person skilled in the art to practice the invention, including making and using any devices or systems and performing any related or incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

The invention claimed is:

1. A method of increasing adult height in an individual suffering from Non-24, the method comprising:
   administering to the individual an effective dose of tasimelteon or a pharmaceutically-acceptable salt thereof before the age of peak growth rate (PGR), thereby entraining the individual to a 24-hour sleep-wake cycle,
   wherein:
   in the case that the individual is female, the age of PGR is about 12 years; and
   in the case that the individual is male, the age of PGR is about 14 years.

2. The method of claim 1, wherein the individual has no light perception.

3. The method of claim 1, wherein administering comprises orally administering to the individual 20 mg of tasimelteon or a pharmaceutically-acceptable salt thereof once daily before a target bedtime.

\* \* \* \* \*